United States Patent [19]

Callahan et al.

[11] 4,152,393

[45] May 1, 1979

[54] REACTOR FOR CONTACTING GASES AND A PARTICULATE SOLID

[75] Inventors: James L. Callahan, Bedford Heights; Harley F. Hardman, Lyndhurst; Ernest C. Milberger, Solon, all of Ohio

[73] Assignee: The Standard Oil Company, Cleveland, Ohio

[21] Appl. No.: 758,607

[22] Filed: Jan. 12, 1977

Related U.S. Application Data

[63] Continuation of Ser. No. 339,082, Mar. 8, 1973, abandoned.

[51] Int. Cl.[2] .............................. B01J 8/26; B01J 8/36

[52] U.S. Cl. .................................... 422/144; 208/164; 422/147; 585/444; 585/617; 585/656

[58] Field of Search .................. 23/288 S, 284, 288 E; 208/163, 164

[56] References Cited

U.S. PATENT DOCUMENTS

| | | | |
|---|---|---|---|
| 2,378,342 | 6/1945 | Voorhees et al. | 23/288 S X |
| 2,477,751 | 8/1949 | Johnson | 23/288 S |
| 2,758,066 | 8/1956 | Breckin | 23/288 S X |
| 3,721,530 | 3/1973 | Bouchet | 23/288 E X |

*Primary Examiner*—Barry S. Richman

*Attorney, Agent, or Firm*—Herbert D. Knudsen; William D. Mooney

[57] ABSTRACT

A reactor that consists of a single shell that contains a reaction zone and a regeneration zone. The reaction zone and regeneration zone are arranged in such a manner that (a) a particulate solid may be transferred by flow of gases from the regeneration zone to the reaction zone by a first route and then back to the regeneration zone by a second route; and (b) the gases passing through the regeneration zone are not transferred to the reaction zone and the gases passing through the reaction zone are not transferred to the regeneration zone.

11 Claims, 2 Drawing Figures

2 3 4 5 2 2 6 7 1 11 AERATOR 13 12 AERATOR 8 REACTANT FEED REGENERATION AIR 9 10 AERATOR (PUMP)

2
3
4
5
2
2
6
7
1
11
AERATOR
13
12
AERATOR
8
REACTANT FEED
REGENERATION AIR
9
10
AERATOR (PUMP)

6
3
7
1
11
8
12
9

REACTOR FOR CONTACTING GASES AND A PARTICULATE SOLID

This is a continuation, of application Ser. No. 339,082 filed Mar. 8, 1973, now abandoned.

BACKGROUND OF THE INVENTION

U.S. Pat. No. 3,669,877 shows a separated reaction zone and oxidation zone. Open contact between the regeneration zone and the reaction zone of the reactor in this patent, however, does not prevent the mixing of gases in the oxidation and regeneration zones. As a consequence, the reaction product is contaminated with the gases from the regeneration zone. The present invention essentially eliminates this contamination.

Also, U.S. Pat. No. 3,669,877 does not provide an orderly transfer of a solid particulate from the reaction zone to the regeneration zone and back to the reaction zone. In contrast, the present invention provides an orderly and continuous flow of the solid particulate through the reaction zone and the regeneration zone. This continuous flow is accomplished without the transfer of gases between the two zones.

SUMMARY OF THE INVENTION

A new reactor has been discovered in the present invention. This reactor consists of an outer shell that contains a first contact zone called a reaction zone and a second contact zone called a regeneration zone, said reaction zone and said regeneration zone being arranged in such a manner that (a) particulate solid may be transferred by the flow of gases from the regeneration zone to the reaction zone by a first route and back to the regeneration zone by a second route; and (b) the gases passing through the regeneration zone are not transferred to the reaction zone and the gases passing through the reaction zone are not transferred to the regeneration zone. The reactor of the present invention may be used in one embodiment for a reaction that employs a particulate solid that is capable of retaining certain elements of the gas stream in one zone and relinquishing those elements in another zone. For example, in the oxidation of propylene to acrolein, an appropriate catalyst could be oxidized in a regeneration zone by acquiring and retaining oxygen from air, and in the reaction zone, a feed consisting of propylene is introduced, and the catalyst reqlinquishes its retained oxygen, oxidizing propylene to acrolein. The reactor effluent contains only unreacted propylene and products, whereas in the art reactions, large amounts of inert gases are part of the effluent. In a similar manner, copper oxide could be reduced to copper metal with a stream of hydrogen in a regeneration zone and then the reduced copper oxide could be transferred to the reaction zone where the reactant is reduced and the reduced copper oxide is oxidized.

The present invention is best understood by reference to the drawing.

DESCRIPTION OF THE DRAWING

Referring to FIG. 1, it is seen that the reactor consists of an outer shell 1 which is a cylinder having a bottom. The outer shell 1 has a top 2 with a downwardly extending concentric wall 3. In the broad description of the invention, top 2 but not concentric wall 3, is a part of the enclosed outer shell. The zone inside of concentric wall 3 is the regeneration zone, and the zone outside of wall 3 is the reaction zone. Cyclone 4 is used for the regeneration zone, and cyclone 5 is used for the reaction zone.

Figure 1:
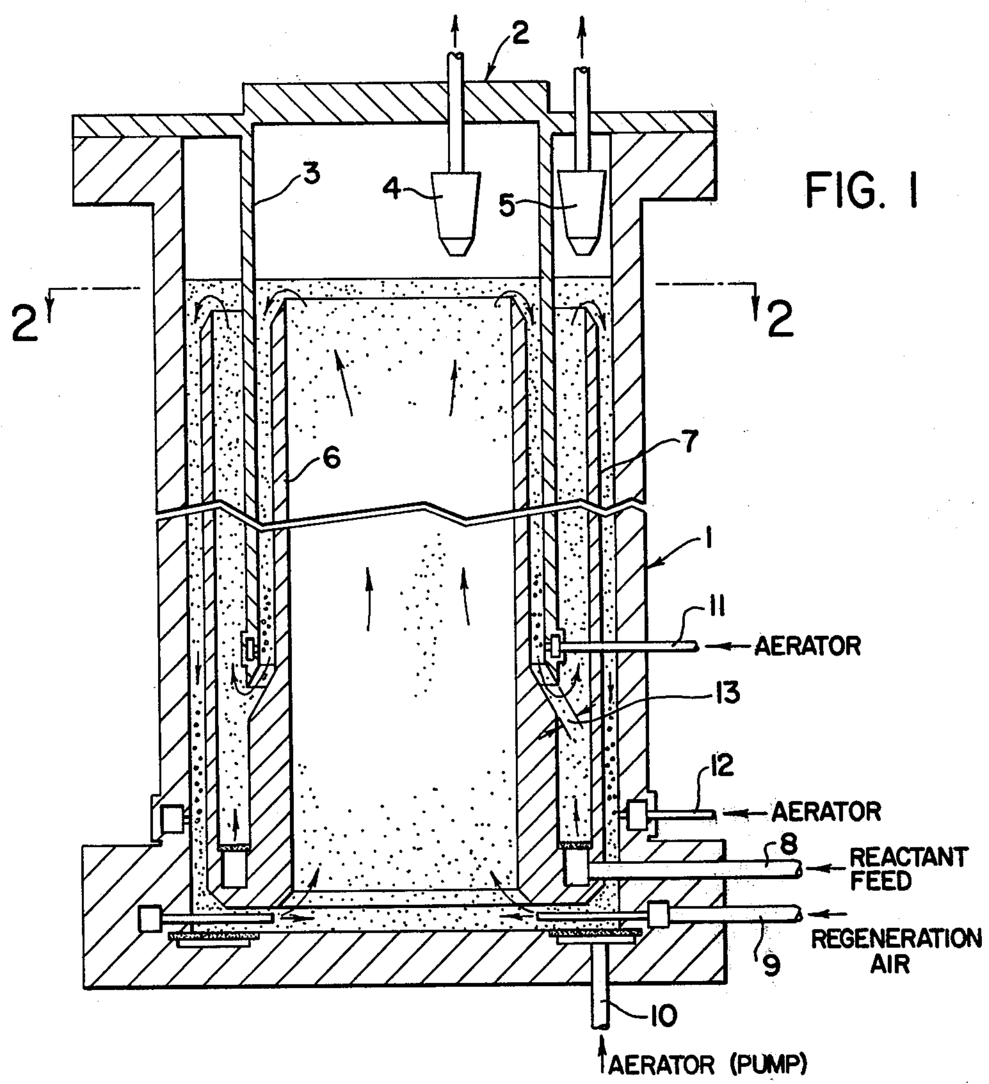
FIG. 1 shows the cross-sectional side view of the reactor.

Inside the shell 1 there is concentric wall 6 and concentric wall 7 having substantially the same height. These two concentric walls in the reactor are connected around the bottom. These walls prevent the mixing of gases from the reaction zone and the regeneration zone while allowing solid to be transferred from one zone to the other. As indicated above, shell 1 and walls 3, 6 and 7 are each cylindrical and concentric with one another. It should therefore be appreciated that shell 1 and walls 3, 6 and 7 are "similar" in the geometric sense.

There is a reactant feed inlet 8 through which reactants are fed into the reactor around the circumference at the bottom between concentric walls 6 and 7. Regeneration air is fed through inlet line 9 and a plurality of nozzles located radially around the circumference of the bottom. This regeneration air feed acts as a pump in this particular reactor by drawing the particulate solid out of the reaction zone and transferring it to the regeneration zone.

In addition to the above components, the reactor has various aerator inlets where small amounts of a gas are fed into the reactor to encourage movement of the particulate solid. These aerators 10, 11 and 12 distribute the gas throughout the circumference of the reactor and are placed in positions where the particulate solid tends to become immobilized.

In the operation of the reactor, the total reactor is filled with a particulate solid to a level above the tops of walls 6 and 7. The particulate solid usually has a diameter of less than about 400 microns for metal oxide solids.

A small air or steam flow is begun through aerators 10, 11 and 12. This flow of gas is not sufficient to cause substantial movement of the particulate solid. Regeneration air is then introduced through line 9. This flow of air acts as a pump and causes the particulate solid to move into the regeneration zone within wall 6 and to become fluidized. Simultaneously, with the beginning of the regeneration air, the reactant feed can be started by passing the reactants into the reactor through line 8.

In the operation of the reactor, the regeneration air passes through the particulate solid oxidizing the solid and then the gas stream remaining is passed through cyclone 4 and out of the regeneration zone. Little or no gas is transmitted through any passage other than the cyclone under proper operating conditions.

In the reaction zone, reactant gas is passed into the reactor through inlet 8, the reactants pass through the oxidized catalyst reacting in the process to form the desired product, and all gas from the reaction zone passes from the reactor through cyclone 5. Little or no gas passes from the reaction zone to the regeneration zone under proper operating conditions.

In the operation of the reactor, the flow of solids through the regeneration zone and the reaction zone is controlled by the flow of gases and the pressures in the two zones. Following the path of the particulate solid from the regeneration zone to the reaction zone and back, it is seen from the drawing that the catalyst begins its movement inside of the concentric wall 6. The particulate solid is carried by the air upward inside of wall 6 and over the top of wall 6. The solid then travels down between wall 6 and wall 3. Gas supplied through aerator 11 facilitates this movement of the solid down between wall 6 and wall 3. When the solid passes spacing 13, it enters into the reaction zone.

The primary reaction zone is formed between wall 3 and wall 7. In this zone, reactant gases from reactant feed 8 cause the solid to move upward and over wall 7 into the zone between wall 7 and the reactor shell 1. In this zone between wall 7 and the reactor shell 1, the solid moves downward with the assistance of a gas stream from aerator 12.

As the particulate solid moves downward past aerator 12, it becomes subject to the pumping action of regeneration air through line 9. Pumping action is achieved by manifolding the regeneration air to a multiplicity of nozzles which act as ejectors utilizing the regeneration air as the motivating fluid. This pumping action draws the catalyst down underneath the connection between walls 6 and 7 and sends it through the regeneration zone inside wall 6. Gas from aerator 10 is instrumental in facilitating this transfer of solid. Thus, the cycle of the particulate solid is complete.

Figure 2:
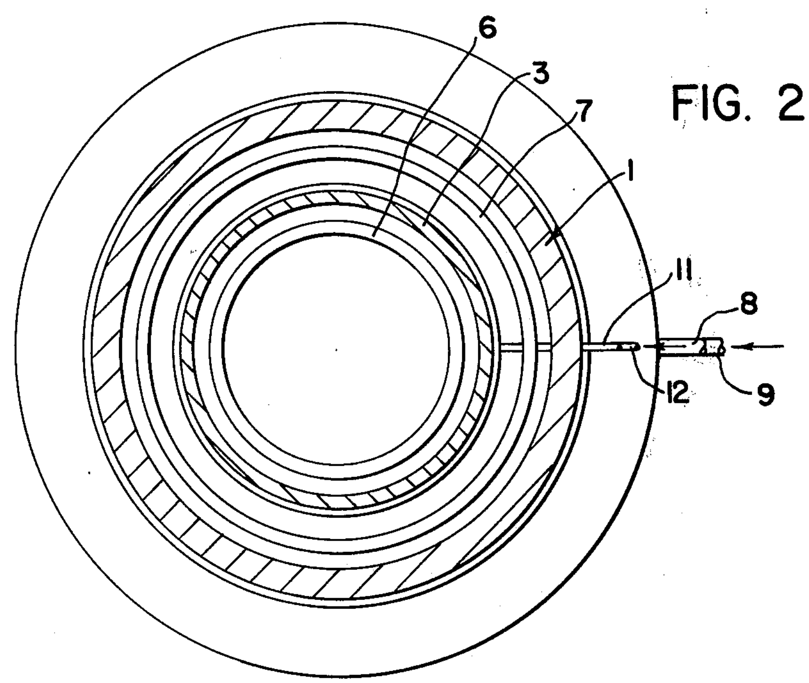
FIG. 2 shows the top view of the same reactor.

Referring to FIG. 2, a top cross-sectional view taken along cross-sectional line 2 is shown. In this view, it is seen that the reactor of the invention consists of a number of concentric walls. Concentric wall 6 is the innermost wall, cross-hatched wall 3 is next to the outside. The solid line just outside of wall 3 shows that aerator 11 extends around the circumference of wall 3.

Wall 7 is the next outer wall. Outer shell 1 is cross-hatched and the adjacent solid line on the outside shows that aerator 12 extends around the circumference of shell 1.

DESCRIPTION OF THE PREFERRED EMBODIMENTS

High rates of solid circulation can be obtained using this invention while at the same time little or none of the gases in the two zones of the shell are mixed with each other. This circulation action provides enough catalyst in an oxidation, ammoxidation or oxidative dehydrogenation reaction to permit running a feed of pure reactants into the reaction zone without the addition of air. For example, in the oxidative dehydrogenation of butenes to butadiene, the reactant feed could be limited to the butene, thus eliminating the air that is normally required. The ramifications of this elimination are very significant. In the oxidative dehydrogenation of butene using air, the air-to-butene ratio is normally about 10/1. In the present invention, the total of 11 volumes of gas that is required in the reaction zone is reduced to one volume. Only the butene is fed, and the 10 volumes of air in the reaction zone are eliminated. Thus the gas fed to the reaction zone for a given amount of capacity can be dramatically reduced. Moreover, the unreacted reactants for recycle and the desired product need be separated only from the by-products rather than the large volume of gas remaining in a normal oxidative dehydrogenation.

The reaction of the present invention may have the design shown in the drawing, or it may have any other design in a single shell which meets the criteria of the present invention: (a) that a particulate solid may be transferred from the regeneration zone to the reaction zone by a first route and back to the regeneration zone by a second route; and (b) that the gases passing through the regeneration zone are not transferred to the reaction zone and the gases in the reaction zone are not transferred to the regeneration zone.

The particular reactor geometry and the distribution and shape of the gas feeds may vary substantially. The contact zones may be open or they could contain cooling coils or sieve trays or any other internal modifications. The detailed design of the pumping system is primarily dependent upon the reactor design, the desired solids circulation rate and the pressure differential in the contact zones.

The reactor can be constructed of essentially any material. Choice of materials is limited only by the nature of the reaction being conducted. Normally, metal reactors are used, but glass or clear plastic models are most helpful for determining the flow rates of solids in the reactor and optimum operation of the reactor. Clear models are also very useful for observing whether "dead" spots are present. Solid that does not circulate in the reactor is unavailable for the desired reaction.

In the practical operation of the reactor of the present invention, the critical variables are: (1) the flow of gases through the reactor; and (2) the differential in the pressure between the reaction zone and the regeneration zone.

Gas flows in the reactor are characterized by the different compositions of the gas and the different purpose of the flow.

The composition of gas flowing through the reaction zone and the regeneration zone is almost always different. Accordingly, the flow rate and direction of the flow should be adjusted so that the mixing of the gases of different composition is minimized. Using this criterion, a flow of the reactant propylene in the oxidation of propylene to acrolein would not be directed in a manner that the propylene would escape the reaction zone and be combined with the gases in the oxidation zone.

The purpose of the flow of gas also differs. The flow of gas from a particular gas inlet can be used to provide for movement of the particulate solid through the communicating passageways, or it can be used to provide fluidization for the particulate solid. The main difference between these two flows is the velocity of the gas. The velocity of the gas that provides transfer of the solid is substantially higher than the velocity of the gas that provides fluidization.

The transfer of solids throughout the reactor is normally accomplished by high velocity gas flows directed in the desired path of flow. Conveying the particulate solid around corners in the reactor, however, is most conveniently accomplished by eduction where the particulate solid is drawn from one portion of the reactor and transferred through an angular channel to another portion of the reactor. Referring to FIG. 1, the eduction is provided by the regeneration air pumped through 9. This regeneration air draws the particulate solid from the reaction zone and transfers it around a corner to the regeneration zone.

The gas flow of the aerators is to maintain fluidization and is also important. Increased fluidization by means of aerators should be provided in areas where the particulate solid does not follow a straight-line path and in areas where the particulate solid transverses a narrow passageway. It has been found that increased fluidization is especially important in areas where eduction takes place. Referring to FIG. 1, this fluidization is provided by aerator 10. The dramatic impact of the fluidization of this eductor is shown in the Specific Embodiments. In Table I, Examples 7–9 show the effect of different degrees of fluidization on the solids turnover rate. As the flow of gas through the aerator is increased, the solids turnover is increased.

In a particular reactor, the desired rate of flow of gases through the reaction zone and the regeneration zone is directly dependent upon the size of the particulate solid needed and the circulation rates required. For any given reaction, catalyst and reactor the desirable flow rates can be readily determined by observation in a clear plastic model or by a minimal amount of experimentation.

The second critical variable in the control of solids flow through the reactor is the pressure differential between the pressure in the gas phase of the regeneration zone as compared to the pressure in the gas phase of the reaction zone. This pressure differential is expressed as follows:

$$\Delta P = P\ \text{regeneration} - P\ \text{reaction}$$

and is stated in terms of inches of water in view of the sensitivity of the solids circulation to this variable. The optimum pressure differential is just on the positive side of 0. As the pressure differential is decreased from a large positive value, the circulation of solids is increased. The circulation of solids should be maximized at a near zero value. As the pressure differential becomes negative, solid circulation is again decreased and finally stops. Negative pressure differentials, however, are undesirable because this means that the gas pressure in the reaction zone is higher than the gas pressure in the regeneration zone. This negative pressure differential causes reactants and products in the reaction zone to be transferred to the regeneration zone where those valuable gases are lost. To assure that no product is lost, a slight positive pressure differential is preferably maintained.

The maximum ΔP that can be tolerated is a function of the reactor configuration, the strength and efficiency of the pump and the depth of the particulate solid in the reactor. Projecting from the small scale of the reactors presently used, it is believed that the ΔP would preferably fall within the range of ±150 inches of water. In the most preferred practice of the invention, the ΔP would be between about 0 and about 150 inches of water.

The flow of gases through the reactor and the pressure differential discussed in detail above, are the critical variables in the operation of the reactor. Other factors that control the operation of the reactor are best adjusted by experimentation with a clear plastic model.

The solid circulation rates obtainable by the reactor of the present invention are surprisingly high. For example, in a small reactor having a catalyst inventory of only about 6 pounds, circulation rates of well over 300 pounds per hour were easily obtained.

The flow of gases through the reactor should be controlled in such a manner that large bubbles of gas in the solid are minimized. Such large bubbles do not have adequate contact with the solid to allow an effective gas-solid reaction to occur. Most preferred are gas flow rates that cause even and continuous flow of the solid particulate from one zone to the other.

Passing of gases between the reaction zone and the regeneration zone is undesirable in the present invention. As noted, proper operation of the reactor of the invention does not permit the passage of gases from one section to the other. Yet, some solids adsorb gases in one section of the reactor and desorb these gases in the other section of the reactor. Thus, even though no gases as such are transferred from the reaction zone to the regeneration zone, there is a mixing of the reactants and regeneration gases due to adsorption of the gases on the solid. This problem may be at least partially rectified by contacting the solid with a gas that desorbs the adsorbed gases as the solid passes from one zone to another. For example, steam could be contacted with the catalyst used in an ammoxidation reaction just as the catalyst leaves the reaction zone. Gaseous reactants and products adsorbed on the catalyst are desorbed by this treatment, and the presence of reactants and products in the regeneration zone is minimized.

The reactor can be used for essentially any situation where gas is contacted with a particulate solid. Preferred is the use of the reactor in solid-gas reactions where the particulate solid is able to acquire and retain a component of one gas stream and then relinquish that component in a second gas stream. Reactions of most interest in the present invention are the oxidation, ammoxidation and oxidative dehydrogenation of hydrocarbons of up to about 20 carbon atoms. These reactions with olefins of 3 to 5 carbons and alkylbenzenes are of greatest interest. In these reactions as noted above, reaction is conducted using the oxygen retained in the oxidized catalyst rather than the addition of air as a reactant. Using this reactor, substantial savings are realized in the space for reaction zone and in the recovery and purification systems.

SPECIFIC EMBODIMENTS

The Reactor

A reactor was constructed of clear plastic tubing according to the design of the drawing. The shell was a tube of 6.50 inches outside diameter and 5.75 inches inside diameter. The wall adjacent to the shell (wall 7 of the drawing) extending upward had an inside diameter of 5.00 inches and an outside diameter of 5.25 inches. The next adjacent wall extending downward from the top (corresponding to wall 3 of the drawing) had an outside diameter of 4.00 inches and an inside diameter of 3.75 inches. The next adjacent wall (corresponding to wall 6 of the drawing) extending upward from the bottom and connected to the other wall extending from the bottom had an inside diameter of 3.00 inches and an outside diameter of 3.25 inches so long as it runs parallel down along the next adjacent outer wall, and then an outside diameter of 4.00 inches beyond the length of the downward extending wall. The overall internal height of the reactor was 24 inches. The top of the reaction zone and the regeneration zone contained filters made of sintered stainless steel.

The air for the regeneration zone was fed through a feed line corresponding to 9 of the drawing. In this position, the regeneration air is a pump and is referred to in the examples as the pump. Likewise, the aerator 10 will be referred to as the pump aerator. The pump aerator head and reactant feed head were sintered stainless steel.

The reaction zone and regeneration zone downflow aerators consist of a hollow ring with 0.013-inch diameter drilled holes spaced ⅝ inch apart. The regenerator air was fed through a pump system which was 30 tubes or nozzles spaced radially around the circumference of the reactor at essentially equal intervals. These tubes were 1/16 inch outside diameter, 0.045 inch inside diameter and 1⅛ inch long and were connected to a common gas supply.

EXAMPLES 1-12 — Effect of Gas Flow Rates on Solids Turnover

The reactor was filled with 2950 g. of a solid metal oxide that had a particle size between about 44 and about 177 microns. The spacing between the regeneration zone and the reaction zone, spacing 13, was adjusted to 0.75 inch.

The reactor was run at various gas flow rates for the pump, the reactor and the pump aerator. The regeneration aerator (corresponding to 11 of the drawing) was run at 2.2 ft.$^3$/hr., and the reactor aerator (corresponding to 12 of the drawing) was run at 2.6 ft.$^3$/hr. Air was used as feed through all inlets of the system.

The solids turnover rate was measured by visual observation of the rate of downflow of solid in the chamber closest to the shell. From this rate of downflow plus knowledge of the volume in this outside chamber and the density of the solid, the solid turnover rate was calculated. At given flow rates, the values obtained were reasonably reproducible. The results of these various air flow rates at a $\Delta P$ of 0 in. $H_2O$ are shown in Table I.

Table I

| | Turnover Rate for Various Flows | | | |
|---|---|---|---|---|
| | Flow Rates, ft.3/hr. | | | |
| Example | Pump | Reactor | Pump Aerator | Solids Turnover Rate, lb./hr. |
| 1 | 36 | 12.4 | 1.5 | 0 |
| 2 | 60 | 12.4 | 1.5 | 34 |
| 3 | 80 | 12.4 | 1.5 | 57 |
| 4 | 100 | 12.4 | 1.5 | 109 |
| 5 | 80 | 12.4 | 3 | 149 |
| 6 | 80 | 21.1 | 3 | 220 |
| 7 | 80 | 37 | 3 | 283 |
| 8 | 80 | 37 | 1.5 | 176 |
| 9 | 80 | 37 | 4.5 | 315 |
| 10 | 80 | 12.4 | 4.5 | 142 |
| 11 | 36 | 37 | 1.5 | 34 |
| 12 | 100 | 37 | 1.5 | 202 |

EXAMPLES 13-15 — Solids Turnover at Narrower Spacing between Zones

The spacing 13 between the regeneration zone and the reaction zone was narrowed from ¾ inch to ¼ inch. The effect on solids flow at a $\Delta P$ of 0 in. $H_2O$ is shown in Table II. The flow of gas through the pump was maintained at 80 ft.$^3$/hr. and flow through the pump aerator was 3.0 ft.$^3$/hr.

Table II

| Effect of Change in Spacing Between Zones | | | |
|---|---|---|---|
| | Gas Rate | Solids Turnover, lb./hr. | |
| Example | of Reactor, ft.$^3$./hr. | ¼ spacing | ¾ spacing* |
| 13 | 12.1 | 100 | 149 |
| 14 | 20.8 | 140 | 220 |
| 15 | 36 | 180 | 283 |

*At closest reactor gas flow rate from Table I

EXAMPLES 16-22 — Effect of Pressure Differential on Solids Turnover

The pressure in the gas phase of the regenerator less the pressure in the gas phase of the reactor has been defined as $\Delta P$ or the pressure differential. As noted, this pressure differential has a substantial impact on the solids turnover.

To obtain these data, the reactor was run under the following gas feed rates: pump 80 ft.$^3$/hr., reactor 30 ft.$^3$/hr. and pump aerator 3 ft.$^3$/hr. The pressure in the regeneration zone was then varied by restricting flow of air through regeneration zone exit causing an increase in the pressure of the gas phase in the regeneration zone and the consequent positive $\Delta P$. The effect of different $\Delta P$ values is shown in Table III.

Table III

| Effect of $\Delta P$ on the Solids Turnover | | |
|---|---|---|
| Example | $\Delta P$, in. $H_2O$ | Solids Turnover Rate, lb./hr. |
| 16 | 0 | 259 |
| 17 | 1.0 | 202 |
| 18 | 1.5 | 151 |
| 19 | 2.0 | 130 |
| 20 | 3.0 | 95 |
| 21 | 4.0 | 72 |
| 22 | 5.0 | 70 |

It can be seen from Table III that optimum solids turnover is obtained at a $\Delta P$ of zero. It will be remembered, however, that the $\Delta P$ value should remain on the positive side to prevent the transfer of gases from the reaction zone to the regeneration zone.

EXAMPLES 23-31 — Gas Leakage between Zones at Various Flow Rates

To determine the disposition of gases fed into the reactor, air was fed through all gas input lines except one. In this one line, $CO_2$ was fed, the effluents of both zones were then analyzed for $CO_2$. The gas distribution is defined as that percent of the $CO_2$ going to the regeneration zone or the percent of $CO_2$ going to the reaction zone from a given inlet.

At a $\Delta P$ of 0 in. $H_2O$ the reactor was run at various solid turnover rates using a ¾ inch spacing 13 between zones while $CO_2$ was injected at different places. The results of these tests are shown in Table IV.

Table IV

| Distribution of Gases Fed to Reactor | | | | |
|---|---|---|---|---|
| | | $CO_2$ | Gas Distribution, % | |
| Example | Solid Turnover Rate, lb./hr. | Injection Point | Reaction | Regeneration |
| 23 | 34 | Pump | 0.05 | n.d. |
| 24 | 34 | Reactor | n.d. | 16.7 |
| 25 | 34 | Pump Aerator | 50.5 | 49.5 |
| 26 | 149 | Pump | 0.9 | n.d. |
| 27 | 149 | Reactor | n.d. | 15.5 |
| 28 | 149 | Pump Aerator | 92.4 | 7.6 |
| 29 | 314 | Pump | 0.5 | n.d. |
| 30 | 314 | Reactor | n.d. | 0.5 |
| 31 | 314 | Pump Aerator | 14.7 | 85.3 |

n.d. = no data (it is assumed that the remainder to make 100% went to this zone).

EXAMPLES 32-33 — Reactor to Regenerator Leakage Using a ¼ Inch Spacing at Various Flow Rates Using a ¼ inch spacing between the regeneration zone and the reaction zone rather than the ¾ inch spacing of Examples 23-31 above, gas leakage from the reactor feed to the regenerator were determined at the flow rates of Examples 13 and 14. The gas leakage from the reaction zone to the regeneration zone using a flow rate of 100 lbs./hr. (Example 13) was 5.1% at a $\Delta P$ of 0. At a flow rate of 140 lbs./hr. (Example 14) the gas leakage was 1.6%.

EXAMPLE 34 — Effect of $\Delta P$ on Gas Leakage

The reactor was run under steady conditions at a $\Delta P$ of zero. The gas leakage from the reactor to the regenerator from the $CO_2$ being fed into the reactor was 8.2%. The $\Delta P$ was raised to one inch of $H_2O$, and the leakage was reduced to 3%.

EXAMPLE 35 — Ammoxidation of Propylene Using Oxidant Reactor

A metal reactor as described above was constructed. A fluid bed oxidant having the composition 50% $K_{0.1}Ni_{2.5}Co_{4.5}Fe_3BiP_{0.5}Mo_{12}O_x$ where x is the number of oxygens to satisfy the valence requirements of the other elements present, and 50% $SiO_2$ was used as the particulate solid. The oxidant had a particle size between 74 and 177 microns.

To the reactor was added 2875 g. of the oxidant. This amount of catalyst covered the upward extending walls by about ¼ inch. Under a continuous flow of air through the reactor, regenerator air inlet and reactant inlet and flow of steam through all three aerators, the temperature of the reactor was brought to 523° C.

At reaction temperature, the catalyst turnover was 90,800 g./hr., the pump feed rate was 90.8 ft.$^3$/hr., the pump aerator feed rate was 4.3 ft.$^3$/hr. and the reactor feed rate was 20.3 ft.$^3$/hr. In addition, a very slow feed of steam was maintained to the other two aerators. The $\Delta P$ of the reactor was 0.5 ± 0.5 in. $H_2O$.

Under these steady-state conditions, the feed of air to the reactor was switched to a mixture of propylene and ammonia in the ratio of 1:1.2. The reaction zone effluent was recovered and analyzed. The % conversion of the propylene is stated as the amount of propylene reacted over the amount fed times 100. The % selectivity is the amount of acrylonitrile formed over the amount of propylene reacted times 100. The % per pass conversion is the product of the percent conversion times the percent selectivity divided by 100.

The % conversion of the propylene was 89.0%, the selectivity to acrylonitrile was 64.4% and the per pass conversion to acrylonitrile was 57.3%. The effluent of the regeneration zone was analyzed for products and reactants of the reaction. Only a trace of organic compounds was found in this regeneration zone effluent.

EXAMPLE 36 AND COMPARATIVE EXAMPLE A — Comparison of Effluent from Art to Effluent of the Invention in Ammoxidation The composition of the effluent from the ammoxidation reactor of Example 35 is compared in Table V to the composition of the effluent when propylene, ammonia and air are fed into the reactor in a ratio of 1:1.1:10 over a catalyst to obtain a 97.3% conversion of the propylene, a selectivity for acrylonitrile of 68.7 and a total per pass conversion to acrylonitrile of 66.8%. These data show that in the dry reactor effluent, the concentration of the desired acrylonitrile product is increased more than fivefold as compared to the art. Recovery of the acrylonitrile from this more concentrated stream is much more convenient.

Table V

Effluent Gas Comparison

| | Concentration of Gas in Dry Effluent, Mole % | |
|---|---|---|
| Gas | Comparative Example A (Art ammoxidation) | Example 36 (Oxidant of Invention) |
| Acrylonitrile | 6.3 | 34.3 |
| Acetonitrile | 0.2 | 5.1 |
| Propylene | 0.3 | 3.7 |
| HCN | 0.6 | 0.7 |
| $NH_3$ | 0.1 | 11.7 |
| $O_2$ | 1.5 | 0 |
| $N_2$ | 86.0 | 10.7 |
| CO | 1.8 | 4.1 |
| $CO_2$ | 3.1 | 29.1 |

In the same manner as shown by the example above, other catalytic reactions can be conducted using this catalyst. For example, propylene can be converted to acrolein or acrylic acid; butene can be converted to butadiene; p-xylene can be converted in the presence of ammonia to terephthalonitrile; alkanes, such as propane, butane or isopentane can be converted to olefins; ethylbenzene can be converted to styrene; methanol can be converted to formaldehyde; o-xylene can be converted to phthalic anhydride; ethylene or propylene can be converted to the corresponding oxide; coal could be gasified; or solids could be retorted. In addition to these uses, any other solid-gas reaction can be conducted where the solid is capable of acquiring components of a gas in one zone, retaining those components while being transferred to a second zone and relinquishing those components in the second zone to a different gas stream.

We claim:

1. A reactor for effecting separate and successive contact of a particulate solid with a first gas stream and a second gas stream without substantial mixing of said gas streams comprising:

an enclosed shell having a top, a bottom and side surfaces therebetween, said enclosed shell having a predetermined horizontal cross section, a first wall inside said shell attached to said top and extending downward into said shell thereby defining a first contact zone between the side surfaces of said shell and said first wall and a second contact zone inside said first wall, said second contact zone being separated from said first contact zone at said top, a second wall intermediate the side surfaces of said shell and said first wall thereby dividing said first contact zone into inner and outer first contact zones, a third wall inside said first wall thereby dividing said second contact zone into inner and outer second contact zones, said second and third walls being joined to one another below the bottom of said first wall so as to provide a first clearance between the bottom of said first wall and the junction of said second and third walls and a second clearance between said junction and the bottom of said shell, said second clearance defining an essentially horizontal flow path for particulate solid between said outer first contact zone and said inner second contact zone, first supply means for supplying said first gas stream to said inner first contact zone for effecting fluidization of particulate solid therein and transfer of particulate solid from said inner first contact zone to said outer first contact zone, second supply means for supplying said second gas stream to said inner second contact zone for effecting fluidization of particulate solid therein and transfer of particulate solid from said inner second contact zone to said outer second contact zone, said second supply means being arranged in said second clearance to inject said second gas stream in a generally horizontal direction therein so as to transfer particulate solid from said outer first contact zone through said second clearance and into said inner second contact zone, first gas removal means for removing said first gas from said first contact zone, and second gas removal means for removing said second gas from said second contact zone.

2. The apparatus of claim 1 further comprising first aerator means for supplying air to said second clearance.

3. The apparatus of claim 1 wherein the heights of said second and third walls are essentially equal.

4. The apparatus of claim 1 wherein said second supply means is located at the bottom of said inner second contact zone.

5. The apparatus of claim 1 wherein said first supply means is located at the bottom of the said inner first contact zone.

6. Apparatus according to claim 1 wherein said first and second gas removal means each comprise means for separating a particulate solid from a gas.

7. The apparatus of claim 6 wherein said first and second gas removal means each comprise cyclones.

8. The apparatus of claim 6 wherein the heights of said second and third walls are essentially equal.

9. The apparatus of claim 6 wherein the side walls of said shell, said first wall, said second wall and said third wall are generally vertical and parallel.

10. The apparatus of claim 9 wherein the horizontal cross sections of said shell, said first wall, said second wall and said third wall are similar.

11. The apparatus of claim 10 wherein the horizontal cross sections of said shell, said first wall, said second wall and said third wall are circles.

* * * * *